(12) United States Patent
Kuo

(10) Patent No.: US 6,844,434 B2
(45) Date of Patent: Jan. 18, 2005

(54) SYNTHESIS OF TEMOZOLOMIDE AND ANALOGS

(75) Inventor: Shen-Chun Kuo, Union, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/050,768

(22) Filed: Jan. 16, 2002

(65) Prior Publication Data

US 2002/0133006 A1 Sep. 19, 2002

Related U.S. Application Data

(60) Provisional application No. 60/262,464, filed on Jan. 18, 2001.

(51) Int. Cl.$^7$ .................... C07D 257/12; C07D 233/91
(52) U.S. Cl. .................................... 544/179; 548/326.5
(58) Field of Search ...................... 544/179; 548/326.5

(56) References Cited

U.S. PATENT DOCUMENTS 5,260,291 A   11/1993   Lunt et al. .................. 514/183

FOREIGN PATENT DOCUMENTS

| EP | 0 113 570 A1 | * | 7/1984 |
| EP | 02 252 682 | | 7/1987 |
| GB | 2 125 402 | | 8/1983 |

OTHER PUBLICATIONS

Wang, et al., "Alternative Syntheses of the antitumor drug temozolomide avoiding the use of methyl isocyanates", Journal of Chemical Society, Chemical Communication, Chemical Society, Letchworth, GB, p. 1687–1688 (1994).

Wang, et al., "Antitumor imidazotetrazines. Part 33. new syntheses of the antitumor drug temozolomide using 'masked' methyl isocyanates", J. Chem. Soc., Perkin Trans. 1(21):2783–2787 (1995).

Wang, et al., "Synthetic studies of 8–carbamoylimidzo–'5, 1–D!–1, 2, 3, 5–tetrazi n–4(3H)– one: a key derivative of antitumor drug temozolomide", Bioorg. Med Chem. Lett., 6(2):185–188 (1996).

Yongfeng Wang, "A new route to the antitumor drug temozolomide, but not thiotemozolomide", Chem. Commun., 4:363–364 (1997).

Wang, et al., "Antitumor Imidazotetrazines. 35. New Synthetic Routes to the Antitumor Drug Temozolomide", J. org. Chem. 62(21):7228–7294 (1997).

Newlands, E.S., et al., "Temozolomide: a review of its discovery, chemical properties, pre–clinica development and clinical trials", Cancer Treat. Rev. , 23(1):35–61 (1997).

Wang, et al., Antitumor Imidazotetrazines. Part 36. Conversion of 5–Amino–Imidazole–4–Carboxamide to . . . Journal of the Chemical Society, Perkin Transactions 1, Chemical Society, Letchworth, GB, 10:1669–1675 (1998).

* cited by examiner

*Primary Examiner*—Venkataraman Balasubramanian
(74) *Attorney, Agent, or Firm*—William Y. Lee

(57) ABSTRACT

This invention relates to a novel process for the synthesis of temozolomide, an antitumor compound, and to intermediates useful in this novel process.

21 Claims, No Drawings

SYNTHESIS OF TEMOZOLOMIDE AND ANALOGS

REFERENCE TO RELATED APPLICATIONS

This application claims the benefit of U.S. Provisional Application Ser. No. 60/262,464 filed Jan. 18, 2001.

FIELD OF THE INVENTION

This invention relates to a novel process for the synthesis of temozolomide, an antitumor compound, and analogs thereof, and to intermediates useful in this novel process.

BACKGROUND OF THE INVENTION

Temozolomide, 3-methyl-8-aminocarbonyl-imidazo[5,1-d]-1,2,3,5-tetrazin-4(3H)-one, is a known antitumor drug; see for example Stevens et al., *J. Med. Chem.* 1984, 27, 196–201, and Wang et al., *J. Chem. Soc., Chem. Commun.*, 1994, 1687–1688. Temozolomide, the compound of formula 1:

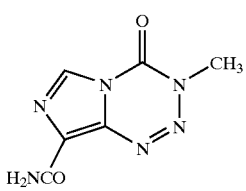

is described in U.S. Pat. No. 5,260,291 (Lunt et al.).

The synthesis of 1 by the process described in *J. Med. Chem.* 1984, 27, 196–201 is depicted in the scheme I below.

Scheme I

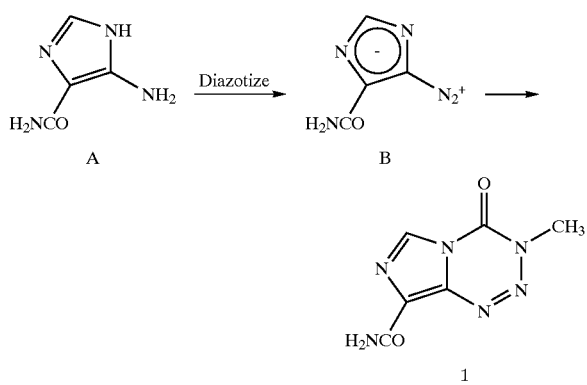

In this process, 5-amino-1H-imidazole-4-carboxamide (A) is converted into 5-diazo-1H-imidazole-4-carboxamide (B), which is then cyclized with methylisocyanate in dichloromethane to provide a high yield of temozolomide. However, this process requires isolation of the unstable and potentially dangerous 5-diazo-1H-imidazole-4-carboxamide (B). Moreover, methylisocyanate is a difficult reagent to handle and ship, especially on the industrial scale, and indeed is better avoided in industrial manufacture. Furthermore, the cycloaddition of methylisocyanate requires a very long reaction time: Table I in *J. Med Chem.* 1984, 27, 196–201, suggests 20 days. Additionally, Stevens et al mention that the cycloaddition of the methylisocyanate to the compound of the formula (B) can proceed through two different intermediates:

The production of I by the two processes described in *J. Chem. Soc., Chem. Commun.*, 1994, 1687–1688 provides a low overall yield from 5-amino-1H-imidazole-4-carboxamide (A): less than 20% (unoptimized—about 17% through 5-diazo-1H-imidazole-4-carboxamide (B) and about 15% through 5-amino-N$^1$-(ethoxycarbonylmethyl)-1H-imidazole-1,4-dicarboxamide (C)); Scheme II below:

Scheme II

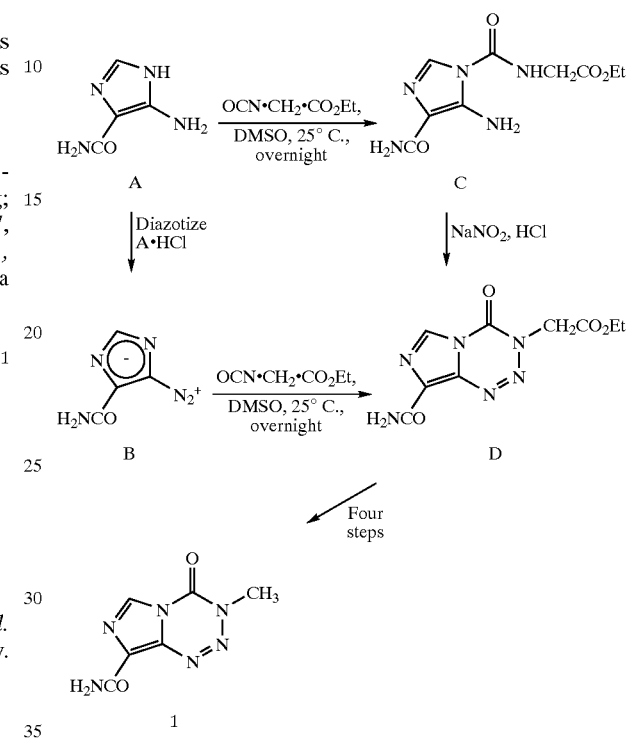

Moreover, the unstable 5-diazo-1H-imidazole-4-carboxamide (B) still has to be isolated in the branch of this process that uses it as an intermediate.

Clearly, therefore, there is a need for synthetic methods that:
a) are more convenient and higher yielding, especially on commercial scale;
b) approach the synthesis of the temozolomide nucleus in novel ways; or
c) improve the preparation or use of intermediates for the processes.

SUMMARY OF THE INVENTION

The present invention provides processes for the preparation of temozolomide, alkyl analogs thereof and useful intermediates of temozolomide.

In one embodiment, this invention provides a process for the preparation of a compound of the formula IA:

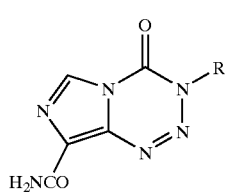

wherein R is an alkyl group having from 1 to 6 carbon atoms, the process comprising, reacting a compound of the formula II:

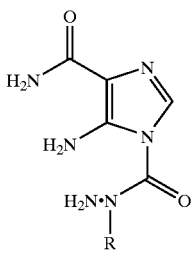

II with a suitable oxidation/cyclization agent in the presence of a soluble iodide, in an inert medium, under an inert atmosphere and at a temperature and for a time sufficient enough to produce a compound of the formula IA.

In another embodiment, this invention provides a process of preparing a compound of formula II by reacting a compound of the formula III:

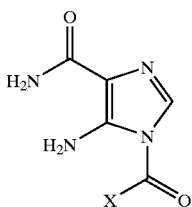

III wherein X is a leaving group of the type that activates its adjacent carbonyl group towards nucleophiles, with a suitable hydrazine, i.e. R—NH—NH$_2$, wherein R is an alkyl group having 1 to 6 carbon atoms.

In another embodiment, this invention provides a process for preparing a compound of the formula III:

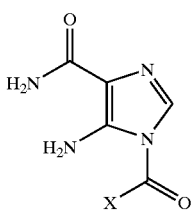

III which comprises reacting a compound of the formula 4:

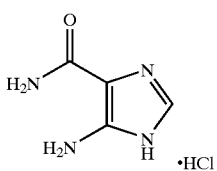

4 with a compound of the formula:

wherein each of X and Y is the same or different leaving group, to yield compound III.

In yet another embodiment, this invention provides a novel process for preparing temozolomide (1):

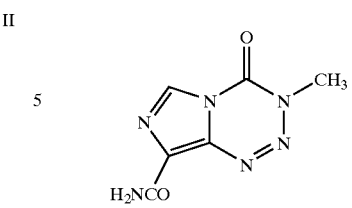

1 comprising:
a) reacting compound 4:

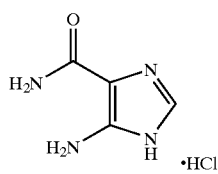

4 with 4-nitrophenyl chloroformate in the presence of triethylamine in CH$_2$Cl$_2$, and under a nitrogen atmosphere at about 25° C. to obtain compound 3:

3

H$_2$N
H$_2$N
4-NO$_2$C$_6$H$_4$O
O;

b) reacting compound 3 with methylhydrazine in DMF at about 0° C. to obtain compound 2:

2

H$_2$NCO
NH$_2$
NH$_2$
CH$_3$ and c) reacting compound 2 with Bu$_4$NI in a 50/50 mixture of THF/CH$_3$CN, at a temperature of about 60° C. for about zero to sixty minutes, followed by the cooling of the reaction mixture to about 25° C. and the addition of H$_5$IO$_6$ with stirring for about 10 to about 60 minutes to obtain temozolomide (1).

The present invention further provides various novel intermediates, specifically:

1-alkyl derivatives of 5-amino-4-(aminocarbonyl)-1H-imidazole-1-carboxylic acid hydrazide wherein the alkyl group contains from 1 to 6 carbon atoms (i.e., alkyl derivatives at the N-1 hydrazine atom), 5-amino-4-(aminocarbonyl)-1H-imidazole-1-carboxylic acid and active esters thereof, especially 4-nitrophenyl 5-amino-4-(aminocarbonyl)-1H-imidazole-1-carboxylate, and 5-amino-4-(aminocarbonyl)-1H-imidazole-1-carboxylic acid 1-methylhydrazide (which can alternatively be named as N$^1$,5-diamino-N-methyl-1H-imidazole-1,4-dicarboxamide).

DETAILED DESCRIPTION

As used herein the following terms have the following meanings unless defined otherwise,

| | |
|---|---|
| DEC.HCl: | 1-[3-(Dimethylamino)propyl]-3-ethyl-carboddiimide hydrochloride |
| DCC: | N,N'-Dicyclohexylcarbodiimide |
| HOBT: | 1-Hydroxybenzotriazole |
| DMF: | N,N-Dimethylformamide |
| EtOAc: | Ethyl acetate |
| NMM: | 4-Methyl morpholine |
| MeOH: | Methyl alcohol |
| EtOH: | Ethyl alcohol |
| Et$_2$O: | Diethyl ether |
| BOC: | t-Boc or tert-Butyloxycarbonyl |
| LiOH: | Lithium hydroxide |
| NaOH: | Sodium hydroxide |
| KOH: | Potassium hydroxide |
| acac | acetylacetonate |
| DCC | dicyclohexylcarbodiimide |
| NCS | N-chlorosuccinimide |
| NBS | N-bromosuccinimide |

The term "alkyl" or "lower alkyl" means straight or branched alkyl chains of 1 to 6 carbon atoms.

"R" is an alkyl chain that can be straight or branched, but is preferably straight, such as for example, 1-pentyl and 1-hexyl. Preferably, it is a lower alkyl group having 1 to 4 carbon atoms, such as 1-butyl, 1-methyl-propyl, 2-methyl-1-propyl, 1-propyl, 1-methyl-ethyl, ethyl or methyl, most preferably methyl.

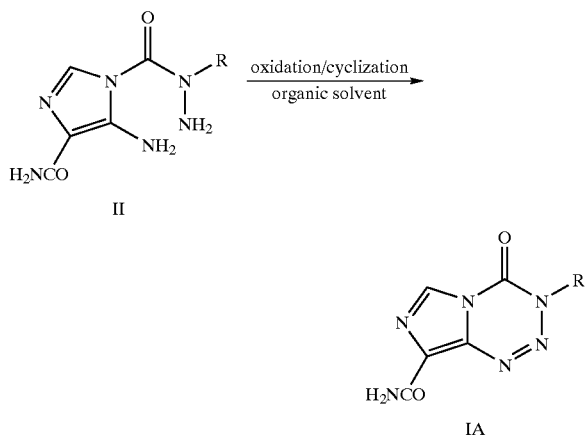

The conversion of the compound of the formula II into the compound of the formula IA (Scheme III) requires concomitant or consecutive oxidation and cyclization to take place. The oxidizing/cyclizing agent may be, for example, periodic acid ($H_5IO_6$), iodine/potassium iodate, bromine or chlorine, or a reagent that oxidizes $NH_2$ to NZ, where Z represents oxygen, (H,Hal), or Hal$_2$, wherein Hal is halogen and wherein the halogen is chlorine, bromine or iodine. Other suitable oxidizing agents include KI/KIO$_3$, I$_2$, I$_2$/KIO$_3$, ICl, ICl$_3$, I$_2$O$_5$, NCS/Me$_2$S, NBS/Me$_2$S, DCC/DMSO/H$_3$PO$_4$, peracetic acid, VO(acac)$_2$/O$_2$, VO(acac)$_2$/t-BuOOH, V$_2$O$_5$, Bu$_4$NI/O$_2$, and MnO$_2$. Preferably, the oxidizing agent is $H_5IO_6$ and the reaction is preformed in the presence of an iodide that is soluble in the reaction medium, the medium being an inert organic solvent. A quaternary ammonium iodide is typically preferred, and examples include tetraalkylammonium iodides such as Bu$_4$NI. However, since the iodide functions catalytically, a small amount of an inorganic iodide, even if only sparingly soluble in the reaction medium, can also be used, i.e. KI.

The process of scheme III is carried out in an inert organic solvent that is selected from a non-nucleophilic solvent such as DMF, an ether, such as t-butyl-methyl-ether, a cyclic ether, such as THF or dioxane, acetonitrile, methylene chloride, toluene, an alkyl alkanoate wherein the alkyl group has 1 to 4 carbon atoms and the alkanoate group has 2 to 4 carbon atoms, i.e. ethyl acetate, and mixtures thereof. The reaction is preferably carried out under an inert atmosphere, e.g., under nitrogen, and at a suitable temperature range from about −20° C. to about +70° C., preferably about 0° C. to about +60° C.

Preferably, the organic solvent is a 50/50 mixture of THF/acetonitrile and since the compound IA is basic, no further acid-binding agent is normally necessary.

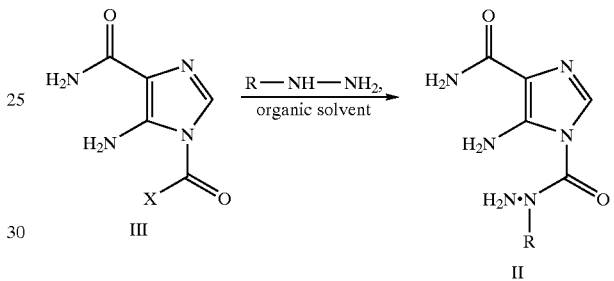

In the preparation of a compound of formula II shown in Scheme IV, compound III is reacted with an alkylhydrazine of the formula R—NH—NH$_2$. R is a lower alkyl as defined above and X is a leaving group of the type that activates its adjacent carbonyl group towards nucleophiles. X may be, for example, an active esterifying group such as a phenyloxy or 2-naphthyloxy group, or a substituted phenyloxy group wherein the substituents are electron withdrawing, e.g., a 2- or especially 4-nitro group, or a pentafluoro group. X may also be, for example, chlorine, bromine or iodine.

The reaction is conducted in an inert organic solvent such as, for example, DMF, THF, CH$_2$Cl$_2$, acetonitrile or mixtures thereof, under an inert atmosphere and at a temperature of about 0° C. Preferably the reaction is conducted under a nitrogen atmosphere, at a temperature of 0° C. using DMF as the solvent.

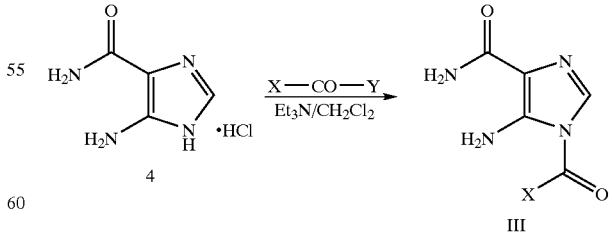

In the preparation of compound III shown in scheme V above, compound 4 is reacted with a compound of the formula:

X—CO—Y wherein X and Y are the same or different leaving group. X or Y can be for example, halogen, phenyloxy, 2-naphthyloxy or a substituted phenyloxy group, wherein said substituents on said phenyloxy groups are, for example, nitro, pentafluoro, chlorine, bromine, iodine or combinations thereof. Preferably, X and Y are different i.e. Y is halogen and X is a phenyloxy, 2-naphthyloxy or a substituted phenyloxy group. More preferably, Y is a halogen such as, for example, bromine, chlorine, or iodine with chlorine being most preferred and X is a phenyloxy, 2-naphthyloxy or a substituted phenyloxy group. Yet even more preferred, Y is chlorine and X is a substituted phenyloxy group with said substituents on said phenyloxy groups being nitro or pentafluoro. Still even more preferred, Y is chlorine and X is nitro-phenyloxy. Examples of compounds of the formula X—CO—Y include, but are not limited to, chloroformate and bromoformate esters of reactive leaving groups such as for example 4-nitrophenyl chloroformate.

The reaction is conducted in the presence of an organic or inorganic acid-binding agent such as, for example, a tertiary amine i.e. pyridine, 2,6-lutidine and triethylamine or a base such as, for example, sodium and potassium bicarbonates or carbonates, with triethylamine being the most preferred.

An organic solvent, preferably an inert organic solvent such as, DMF, THF, $CH_2Cl_2$, acetonitrile, and ethyl acetate is used, with $CH_2Cl_2$ being preferred. The reaction is conducted under an inert atmosphere e.g. a nitrogen atmosphere and at a temperature range of about −20° C. to about +50° C.

In a preferred embodiment of this reaction, 5-amino-1H-imidazole-4-carboxamide.HCl (4) is allowed to react with 4-nitrophenyl chloroformate under a nitrogen atmosphere in the presence of triethylamine in $CH_2Cl_2$ to obtain compound 3 (Scheme VI):

Scheme VI

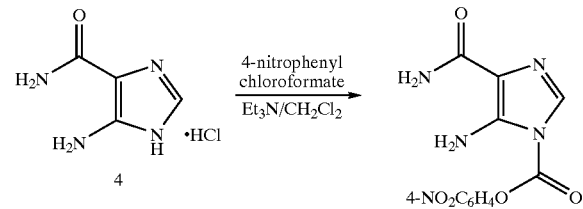

Thus, the present invention provides a novel synthesis for Temozolomide and lower alkyl analogs thereof, which proceeds in three simple steps from a commercially available starting material, 5-amino-1H-imidazole-4-carboxamide.HCl and avoids the use of hazardous materials such as the unstable 5-diazo-1H-imidazole-4-carboxamide and methyl-isocyanate.

A preferred embodiment of the process, directed to the preparation of temozolomide itself, is shown in Scheme VII:

Scheme VII

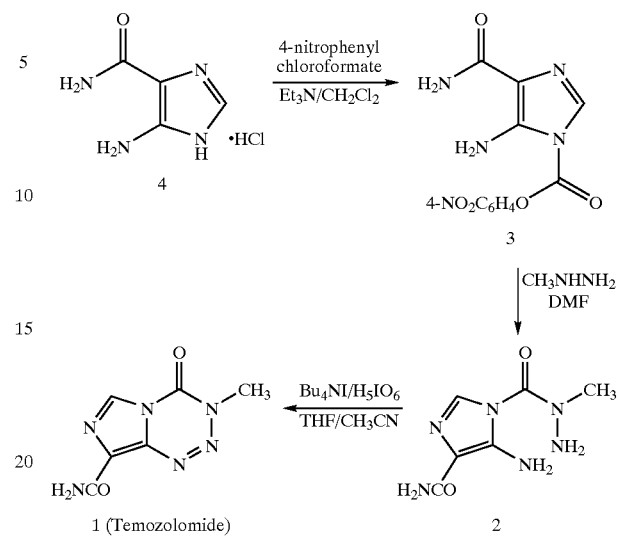

EXAMPLES

The following Examples illustrate but do not in any way limit the present invention. Chemicals obtained from Aldrich Chemical Company (Milwaukee, Wis.) are identified by their catalog number. It should be noted that nomenclature may differ slightly between this specification and the Aldrich catalog.

Example 1

Preparation of Temozolomide (1)

Step A Preparation Compound (3)

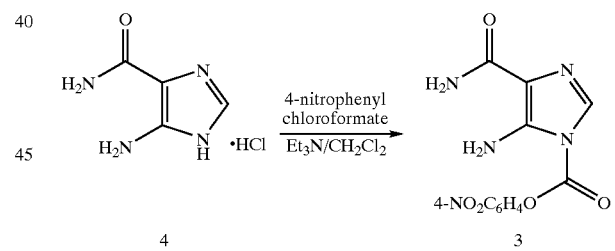

5-Amino-1H-imidazole-4-carboxamide.HCl (4) (25 g, 0.154 mol) (Aldrich 16,496-8), $CH_2Cl_2$ (0.6 L) and $Et_3N$ (45 mL) (Aldrich, 13,206-3) were placed into a dry 2-liter, three-necked flask equipped with dropping funnel, a gas inlet tube, a gas outlet tube, reflux condenser and mechanical stirrer, and maintained under a positive pressure of nitrogen at ambient temperature. The mixture was stirred, and a solution of 400 mL of 4-nitrophenyl chloroformate (34 g, 0.169 mol) (Aldrich, 16,021-0) in $CH_2Cl_2$ was added dropwise. The reaction mixture was stirred vigorously for 4 hours and then left to stand for 18 hours at room temperature. The precipitate was collected by vacuum filtration and washed with $H_2O$ (1.5 L) to afford the product (3) as a pale yellow solid (42 g, 0.144 mol).

$^1$H NMR (400 MHz, DMSO-$d_6$, δ): 8.40 (d, 2H), 7.83 (s, 1H), 7.74 (d, 2H), 7.08 (bs, 1H), 6.95 (bs, 1H), 6.52 (s, 2H).

Step B Preparation of Compound (2)

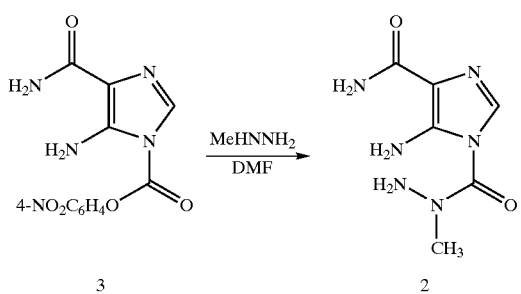

Compound (3) (42 g, 0.144 mol) and DMF (0.27 L) were placed into a dry 1-liter, three-necked flask equipped with dropping funnel, a gas inlet tube, a gas outlet tube, reflux condenser and mechanical stirrer, and maintained under a positive pressure of nitrogen. The reaction mixture was cooled to 0° C., and methylhydrazine (10 mL, 0.188 mol) (Aldrich, M5,000-1) was added dropwise. The reaction mixture was stirred vigorously for 1 hour at 0° C. and was then poured into EtOAc (2.1 L). The precipitate was collected by vacuum filtration and was dried under vacuum (20 mm Hg, room temperature, 18 hours) to afford (2) as a tan solid (27.1 g, 0.137 mol).

$^1$H NMR (400 MHz, DMSO-$d_6$, $\delta$): 7.62 (s, 1H), 6.85 (bs, 1H), 6.75 (bs,1H), 6.00 (s, 2H), 5.10 (s, 2H), 3.15, s, 3H).mp: 188° C. (dec.). Analysis: Calcd for $C_6H_{10}N_6O_2$: C, 36.36; H, 5.09; N, 42.41. Found: C, 36.46; H, 4.99; N, 42.12.

Step C Preparation of Temozolomide (1)

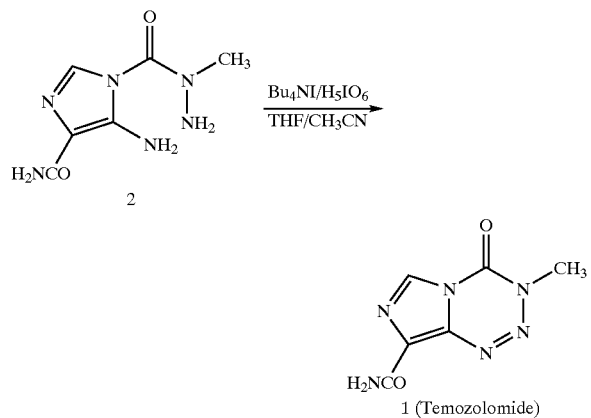

Compound (2) (500 mg, 2.5 mmol), $Bu_4NI$ (95 mg, 0.25 mmol), THF (250 mL) and $CH_3CN$ (250 mL) were placed into a dry 1-liter, three-necked flask equipped with dropping funnel, a gas inlet tube, a gas outlet tube, reflux condenser and mechanical stirrer, and maintained under a positive pressure of nitrogen. The reaction mixture was heated at 60° C. for 20 mm and then cooled to room temperature. $H_5IO_6$ (1.14 g, 5 mmol) was added and the reaction mixture was stirred vigorously at room temperature for 1 hour. The resulting solution was treated with saturated aqueous $Na_2S_2O_3$ (5 mL) and was then concentrated under reduced pressure to dryness. The residue was treated with $CH_3CN$ (200 mL) and was filtered. The filtrate was concentrated and chromatographed on a column of silica gel (1.5% to 2% AcOH/EtOAc) to afford temozolomide (1) (280 mg).

$^1$H NMR (400 MHz, DMSO-$d_6$, $\delta$): 8.80 (s, 1H), 7.80 (bs, 1H), 7.66 (bs, 1H), 3.43 (s, 3H).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for the preparation of a compound of the formula IA:

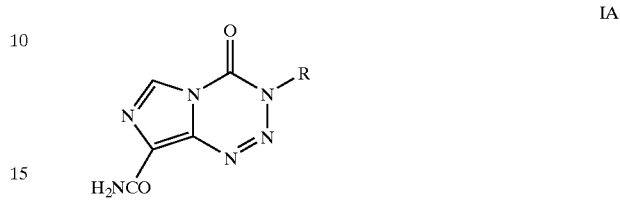

wherein R is an alkyl group having from 1 to 6 carbon atoms, which comprises reacting a compound of the formula II:

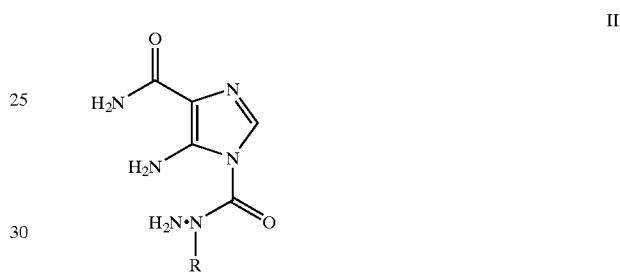

wherein R is described above, with an oxidation/cyclization agent is selected from the group consisting of:
 a) periodic acid,
 b) iodine/potassium iodide,
 c) bromine,
 d) chlorine; and
 e) a reagent that oxidizes $NH_2$ which is adjacent to the group N-R in the compound formula II, to NZ, where Z represents, Oxygen, (H,Hal) or $Hal_2$, and wherein Hal is chlorine, bromine or iodine, wherein said oxidation/cyclization reagent is in the presence of an iodide compound, wherein said iodide compound is quarternary ammonium iodide or inorganic iodide, in an inert organic solvent, under an inert atmosphere and at a temperature, wherein said iodide is soluble in said inert organic solvent, with the proviso that when said oxidation/cyclization agent is not an iodide, the iodide compound itself is the oxidation/cyclization agent.

2. The process of claim 1 wherein R is an alkyl group having 1 to 4 carbon atoms.

3. The process of claim 1 wherein said iodide is selected from the group consisting of $Bu_4NI$ and KI.

4. The process of claim 1 wherein said inert organic solvent is selected from the group consisting of:
 a) an amide;
 b) an acyclic ether;
 c) a cyclic ether;
 d) an alkyl alkanoate wherein the alkyl group has 1 to 4 carbon atoms and the alkanoate group has 2 to 4 carbon atoms;
 e) a halogenated hydrocarbon;
 f) toluene; and
 g) mixtures thereof.

5. The process of claim 4 wherein the organic solvent is selected from the group consisting of:
a) DMF;
b) t-butyl-methyl ether;
c) THF;
d) acetonitrile;
e) methylene chloride; and
f) mixtures of the above solvents.

6. The process of claim 5 wherein the reaction takes place at a temperature of about (−)20° C. to about (+)70° C. and under a nitrogen atmosphere.

7. The process of claim 4 wherein:
a) the organic solvent is a 50/50 mixture of THF/CH$_3$CN;
b) the oxidation/cyclization agent is H$_5$IO$_6$;
c) the iodide is Bu$_4$NI and
d) the reaction takes place at a temperature of about 0° C. to about (+)60° C.

8. A process for preparing a compound of the formula III:

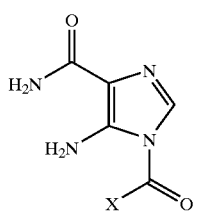

III which comprises reacting a compound of the formula 4:

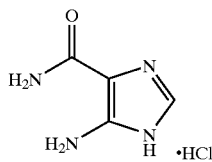

4 with a compound of the formula X—CO—Y in the presence of an acid binding agent, wherein each of X and Y is the same or different leaving group, with the proviso that X is not 4-nitrophenyloxy group, to yield a compound of the formula III, wherein X of said compound X—CO—Y is selected from the group consisting of
a) phenyloxy;
b) 2-naphthyloxy and
c) substituted phenyloxy, and wherein Y of said compound X—CO—Y is selected from:
a) chlorine,
b) bromine, or
c) iodine;
and wherein the substituents on said substituted phenyloxy group are selected from the group consisting of:
a) 2-nitro;
b) pentafluoro;
c) chlorine;
d) bromine;
e) iodine, and
f) combinations of the above.

9. The process of claim 8 wherein said reaction of the compound of the formula 4 with a compound of the formula X—CO—Y is performed in the presence of an acid binding agent, in an inert organic solvent, under an inert atmosphere and at a temperature of about (−) 20° C. to about (+) 50° C.

10. The process of claim 9 wherein said acid binding agent is a tertiary amine.

11. The process of claim 9 wherein the organic solvent is selected from the group consisting of
a) an amide;
b) an acyclic ether;
c) a cyclic ether;
d) an alkyl alkanoate wherein the alkyl group has 1 to 4 carbon atoms and the alkanoate group has 2 to 4 carbon atoms;
e) a halogenated hydrocarbon, and
f) mixtures thereof.

12. A process for the preparation of a compound of the formula II:

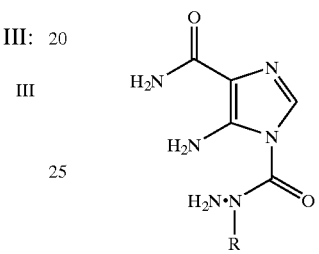

II wherein R is an alkyl group having from 1 to 6 carbon atoms, comprising, reacting a compound of the formula III:

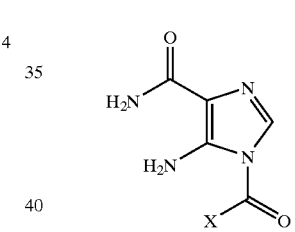

III wherein X is a leaving group with an alkylhydrazine having from 1 to 6 carbon atoms.

13. The process of claim 12 wherein said alkylhydrazine is R—NH—NH$_2$, wherein R is an alkyl group having 1 to 4 carbon atoms.

14. The process of claim 12 wherein the reaction takes place in an inert organic solvent selected from the group consisting of:
a) a non-nucleophilic amine and
b) an ether; and
c) mixtures thereof.

15. The process of claim 12 wherein X is selected from the group consisting of:
a) phenyloxy;
b) 2-naphthyloxy and
c) substituted phenyloxy, wherein the substituents are electron withdrawing.

16. The process of claim 15 wherein said substituents are selected from the group consisting of:
a) 2-nitro;
b) 4-nitro;
c) pentafluoro;
d) chlorine and
e) bromine.

17. The process of claim 13 wherein said compound of formula II is a 1-alkyl derivative of 5-amino-4-(aminocarbonyl)-1H-imidazole -1-carboxylic acid hydrazide wherein the alkyl group contains 1 to 6 carbon atoms.

18. The process of claim 17 wherein said compound of formula II is 5-amino-4-(aminocarbonyl)-1H-imidazole-1-carboxylic acid 1-methylhydrazide.

19. The process of claim 10 wherein compound 4:

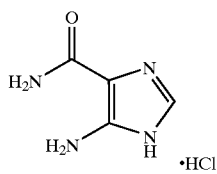

is reacted with 4-nitrophenyl chloroformate, in the presence of triethyl amine, said reaction taking place in methylene chloride solvent, under a nitrogen atmosphere and at a temperature of about (−)20° C. to about (+)50° C. to yield compound (3):

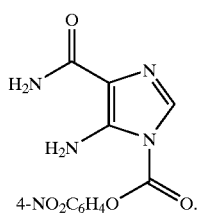

20. A process for preparing temozolomide (1):

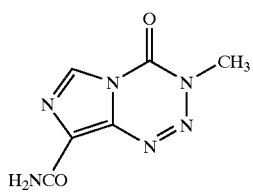

comprising:

a) reacting compound 4:

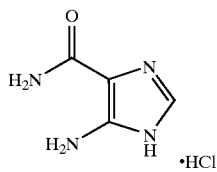

with 4-nitrophenyl chloroformate in the presence of triethylamine in CH$_2$Cl$_2$ under a nitrogen atmosphere at about 250° C. to obtain compound (3):

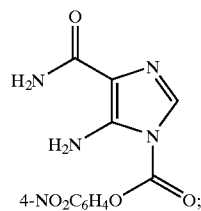

b) reacting compound (3) with methylhydrazine in DMF at about 0° C. to obtain compound (2):

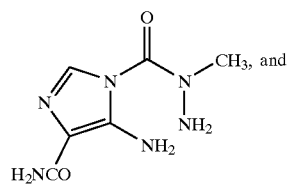

c) reacting compound (2) with Bu$_4$NI in a 50/50 mixture of THF/CH$_3$CN, at a temperature of about (+)60° C. for a time of about 0 to about 60 minutes, followed by the cooling of the reaction mixture to about (+)25° C. and the addition of H$_5$IO$_6$ and stirring for about 10 to about 60 minutes to obtain temozolomide (1).

21. A process for the preparation of compound of the formula IA:

wherein R is an alkyl group having from 1 to 6 carbon atoms, which comprises reacting a compound of the formula II:

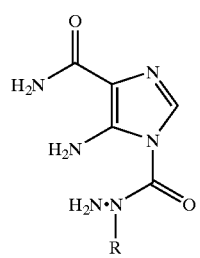

wherein R is described above, with an oxidation/cyclization agent, where said oxidation/cyclization agent is H$_5$IO$_6$, in the presence of an iodide compound, where said iodide compound is Bu$_4$NI, in an inert organic solvent, under an inert atmosphere and at a temperature, wherein said iodide is soluble in said inert organic solvent, with the proviso that when said oxidation/cyclization agent is not an iodide, the iodide compound itself is the oxidation/cyclization agent.

* * * * *

UNITED STATES PATENT AND TRADEMARK OFFICE
CERTIFICATE OF CORRECTION

PATENT NO. : 6,844,434 B2
DATED : January 18, 2005
INVENTOR(S) : Shen-Chun Kuo

It is certified that error appears in the above-identified patent and that said Letters Patent is hereby corrected as shown below:

Column 16,
Line 66, change "250°C" to -- 25°C --.

Signed and Sealed this

Eighth Day of March, 2005

JON W. DUDAS
*Director of the United States Patent and Trademark Office*